United States Patent [19]

Schmidt

[11] 3,988,353

[45] Oct. 26, 1976

[54] PREFERENTIAL REMOVAL OF METALLIC CATALYST FROM EPOXIDATION EFFLUENT

[75] Inventor: John P. Schmidt, Princeton, N.J.

[73] Assignee: Oxirane Corporation, Princeton, N.J.

[22] Filed: June 25, 1975

[21] Appl. No.: 590,290

Related U.S. Application Data

[63] Continuation-in-part of Ser. No. 457,840, April 4, 1974, abandoned.

[52] U.S. Cl.......................................... 260/348.5 L
[51] Int. Cl.².......................................... C07D 301/32
[58] Field of Search ............................. 260/348.5 L

[56] References Cited

UNITED STATES PATENTS 3,523,956    8/1970    Kaplan ........................ 260/348.5 L

*Primary Examiner*—Norma S. Milestone
*Attorney, Agent, or Firm*—Flynn & Frishauf

[57] ABSTRACT

Metallic catalyst is removed selectively from an epoxidation effluent containing the catalyst and acidic materials by contacting the effluent with a specified quantity of an aqueous basic solution to preferentially remove the metallic catalyst therefrom without substantial removal of acidic materials therefrom, and thereafter neutralizing the acidic materials.

7 Claims, 2 Drawing Figures

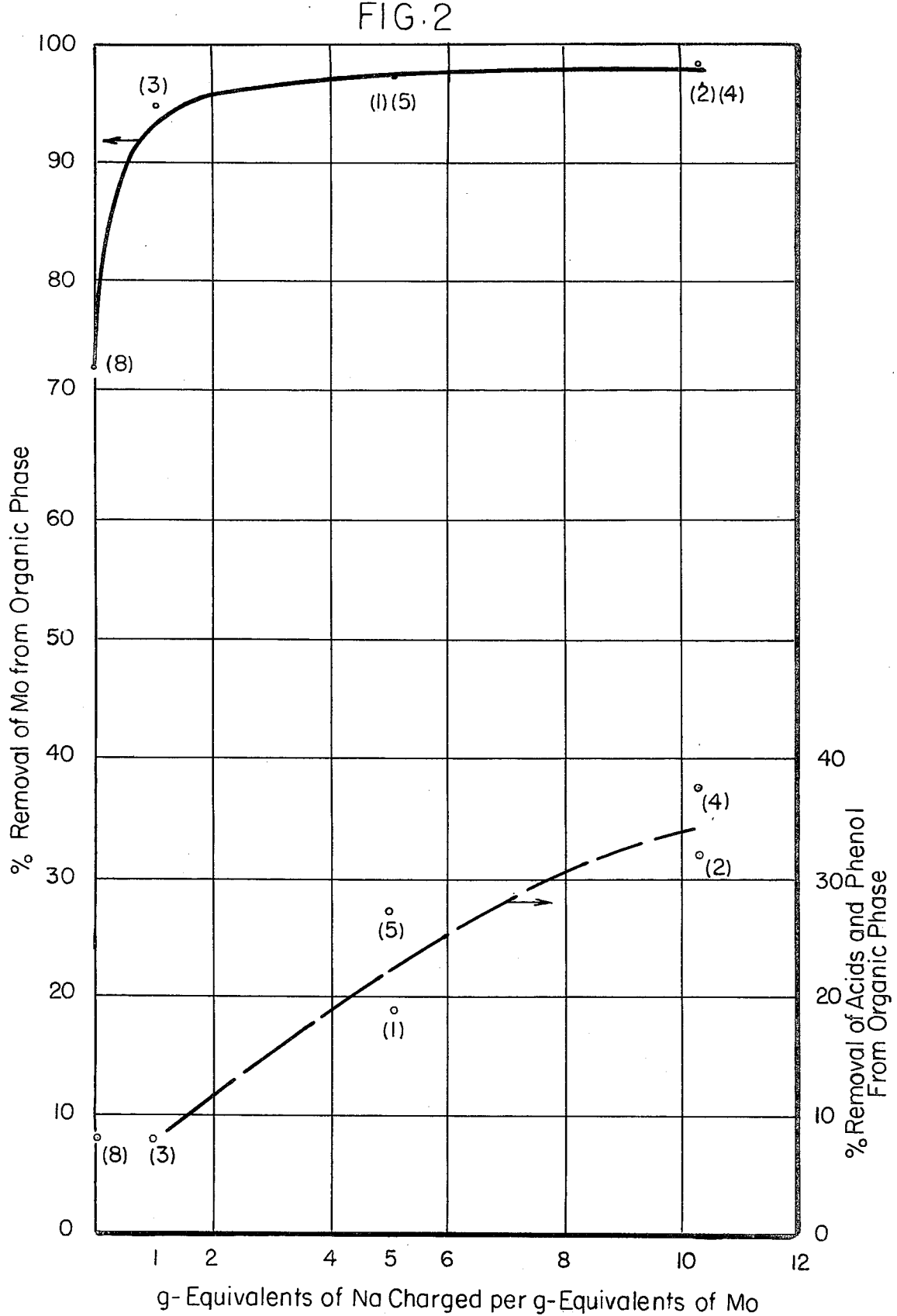

PREFERENTIAL REMOVAL OF METALLIC CATALYST FROM EPOXIDATION EFFLUENT

This is a continuation-in-part of application Ser. No. 457,840, filed Apr. 4, 1974 and now abandoned.

FIELD OF THE INVENTION

This invention has to do with the removal of a metallic catalyst from an epoxidation effluent. More specifically, the invention relates to preferential separation of the metallic catalyst from an epoxidation effluent formed by reaction of an olefin with an organic hydroperoxide in the presence of the catalyst. The effluent contains said catalyst and acidic reaction products.

BACKGROUND OF THE INVENTION

It is well known in the art that metals and metal compounds, preferably heavy metals and compounds thereof, are suitable catalysts for forming oxirane compounds by reaction of olefins with organic hydroperoxides. This is illustrated by U.S. Pat. Nos. 3,351,635; 3,468,099; and 3,375,362. It is also known to remove the catalyst from the reaction product or epoxidation effluent by contacting the effluent with a sufficient quantity of an aqueous basic solution to remove therefrom catalyst in combination with acidic reaction products. This is described in U.S. Pat. No. 3,523,956. In this procedure, there is produced an aqueous waste stream containing salts of the catalyst in admixture with salts of the organic acidic materials.

The procedure described in U.S. Pat. No. 3,523,956 provides a simple method for removing catalyst as well as acidic reaction products from the epoxidation effluent. There is, however, a major drawback with this procedure, as an aqueous waste stream of very large volume is produced containing the metallic catalyst as well as the neutralized acids and phenols. For environmental reasons it is out of the question to discharge this waste stream directly into public waters such as a stream, river, bay or the like. Consequently, some type of waste treatment procedure is required. Further, the problem of waste treatment is technically very complex because of the large waste volume and the conjoint presence of the catalyst and the neutralized acidic materials.

Removal of the organic constituents from aqueous saline wastes is conventionally accomplished by either of two means, incineration or biological degradation. However, attempts to use either method with the waste from the prior process are greatly hindered by the presence of the metallic catalyst. On the one hand, incineration has been found to be unworkable because the incineration equipment becomes fouled with accumulations of solid deposits containing the catalyst, and also because air pollution problems arise through volatilization of some catalyst into the flue gas. Further, the metallic catalyst fouls heat transfer surfaces and makes it impossible to recover useful energy from the incinerator, for example, by generating steam. On the other hand, disposal by biological degradation is also unsatisfactory because of toxic effects of the catalyst on the bacteria population. Thus, elimination of the organic constituents is extremely difficult.

Moreover, even if the organic constituents could somehow be eliminated, there would remain the problem of removing the metallic catalyst, since discharges of heavy metal substances of this type are environmentally restricted. Such removal is impeded by the large volume of water which must be treated to remove small quantities of catalyst, generally much less than one percent.

In addition to the abovementioned environmental disadvantages, the prior process is not amenable to recovery and recycle of potentially valuable chemicals as well as fuel values in the waste stream. The presence of the catalyst strongly hinders attempts to recover and re-use the basic material in the aqueous solution. Additionally, the presence of large quantities of salts of the basic material and the organic acidic materials makes it extremely difficult to recover and re-use the catalyst in the epoxidation process.

The present invention eliminates these difficulties. It has been discovered that by utilizing a two stage procedure, substantially all of the metallic catalyst can be selectively removed in a first stage, and acidic materials neutralized in a second stage. This procedure is surprisingly selective in that one can obtain a relatively small volume of material containing essentially all of the catalyst, in order to have a modest amount of material which can be treated for recovery of the catalyst or disposal of the same.

Therefore, rather than having an environmental problem with a relatively large volume of solution containing all of the metallic catalyst and a large proportion of the acidic/phenolic materials, as obtained in the prior process, the process of this application enables one to produce a relatively small volume of solution containing substantially all of the metallic catalyst but only a small proportion of the acidic/phenolic materials.

Then from the second stage a relatively large volume of material containing the neutralized acids and phenols, with only a small, innocuous catalyst content, can be disposed readily by conventional means, for example, by incineration or biological treatment A particularly preferred option, with major chemical and energy savings, is to treat these neutralized acids and phenols in a fluidized bed incinerator and thereby recover valuable sodium carbonate and sodium bicarbonate.

The two step process of the present invention is therefore much more advantageous than the prior process, on an environmental basis and based on energy savings and recovery of valuable chemicals, despite its greater complexity.

OBJECT OF THE INVENTION

It is a primary object of this invention to remove preferentially the metallic catalyst from an epoxidation effluent containing said catalyst and acidic reaction products.

DRAWINGS

FIG. 2 is a graph showing selective removal of catalyst from an epoxidation effluent.

SUMMARY OF THE INVENTION

Figure 1:
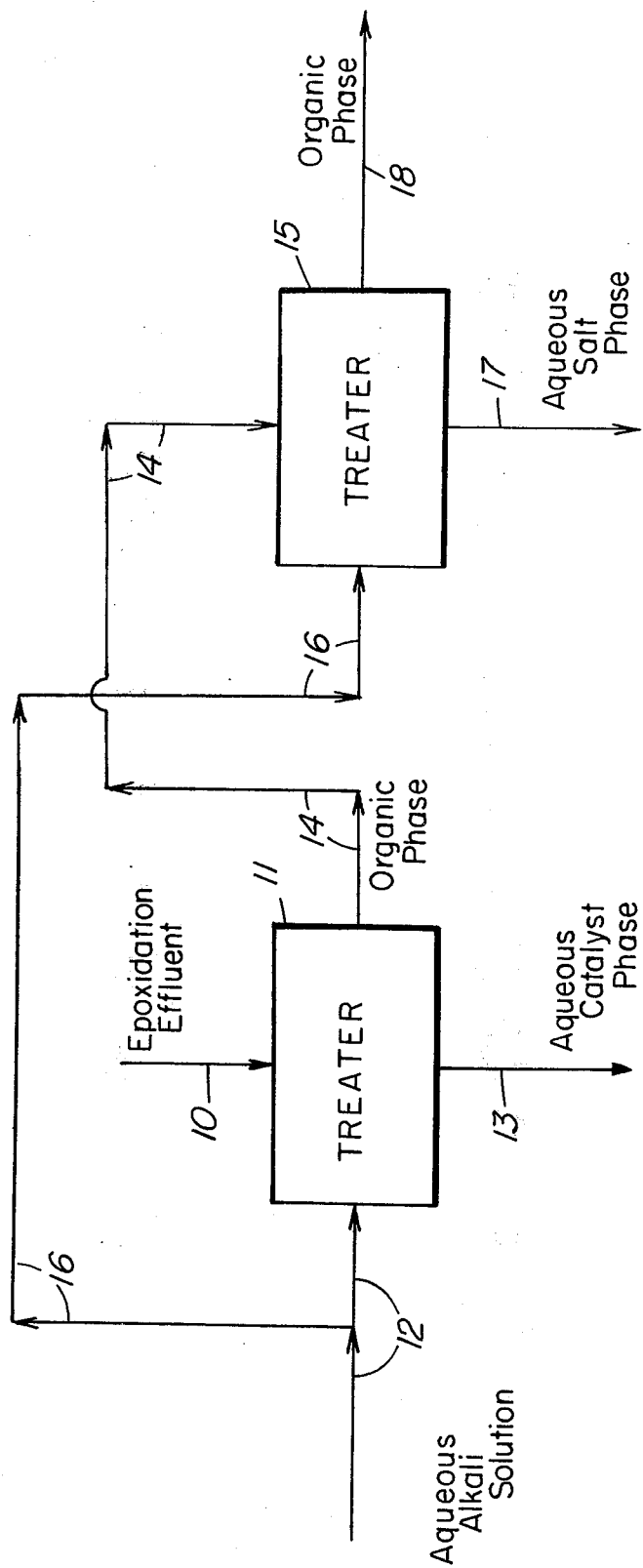
FIG. 1 shows diagrammatically apparatus for conducting the preferential catalyst recovery.

In accordance with the present invention, there is provided a process for preferential removal of a metallic catalyst from an epoxidation effluent containing acidic reaction products and said catalyst. This is accomplished by contacting the effluent with a quantity of an aqueous basic solution sufficient to preferentially and substantially remove all of the metallic catalyst and yet insufficient to remove a substantial quantity of the acidic reaction products therefrom. Acidic reaction products are neutralized in a second step.

SPECIFIC EMBODIMENTS OF THE INVENTION

Olefinically unsaturated reactants, organic hydroperoxide reactants and metallic compounds, which can be used in preparing the epoxidation effluents, are those known in the art as illustrated in said U.S. Pat. Nos. 3,351,635; 3,468,099; and 3,375,362. Quantities of reactants and catalysts and reaction conditions, described in such illustrative patents, are suitable herein. The descriptions of said patents are incorporated herein by reference.

Preferred, however, are effluents prepared by reaction of propylene with ethylbenzene hydroperoxide or cyclohexane hydroperoxide in the presence of molybdenum, tungsten, vanadium and titanium catalysts, with molybdenum constituting a particularly preferred catalyst.

With regard to the aqueous basic solutions used in the process of the present invention, they can be any of those described in said U.S. Pat. No. 3,523,956, and contacting conditions described therein can also be employed. Thus, they may contain a suitable alkali metal or alkaline earth metal compound such as LiOH, NaOH, KOH, $NH_4OH$, $Be(OH)_2$, $Mg(OH)_2$ and/or $Ca(OH)_2$. Oxides, carbonates and bicarbonates of a Group I or II metal of the Periodic Table can also be used. The corresponding ammonium compounds can also be used. It is also contemplated that organic bases such as alkyl amines (e.g. ethanolamines) can be used. The concentration of the alkaline solution can vary from about 0.0001 N up to saturated basic solutions. Preferably, the concentration of the aqueous solution will range from about 0.05 to about 2 N.

As indicated above, the quantity of aqueous basic solution employed is critical. Surprisingly, it has been found that substantially complete removal of metallic catalyst from the reactor effluent can be achieved without removing any substantial amount of organic acidic material, by supplying a quantity of aqueous basic solution that contains only slightly greater than the theoretical proportion of base corresponding to the amount of catalyst present in the effluent. Preferably, the quantity of aqueous basic solution employed contains from about 0.8 to about 10, and most preferably from about 1 to about 3, gram equivalents of base therein per gram equivalent of catalyst present in the effluent.

By way of illustration, when the catalyst employed is molybdenum and the base employed is sodium, a gram-equivalent of base per gram-equivalent of catalyst corresponds to two gram-atoms of sodium per gram-atom of molybdenum.

Generally, the amount of catalyst present in the epoxidation effluent is extremely small compared with the amounts of acidic materials therein such as organic acids and/or phenols. Therefore, the percentage removal of these acidic materials is extremely small even when the quantities of base employed are substantial such as three or four gram-equivalents of base per gram-equivalent of catalyst.

In general, less than 40 percent of the total organic acids and phenols are removed from the epoxidation effluent. Preferably, less than 20 percent, and more preferably, less than 10 percent, are removed.

Reference is now made to FIG. 1 for a particular illustration of the process of this invention.

An epoxidation effluent obtained by the reaction of propylene and ethylbenzene hydroperoxide in the presence of molybdenum, and containing propylene oxide, formic acid, acetic acid, benzoic acid, phenol, ethylbenzene, alpha phenylethanol and dissolved molybdenum, is charged from line 10 to treater 11 wherein it is contacted with a specified amount of an aqueous alkali solution (e.g. NaOH solution) from line 12. As a result of said contact, an aqueous phase containing the molybdenum in solution is formed and is removed from treater 11 through line 13. The solution in line 13 can be treated (not shown) thereafter with a base such as lime to precipitate and recover Mo in solid form, suitable for disposal or sale as a by-product. Alternatively, the Mo can be recovered and recycled to the epoxidation reaction as catalyst.

As indicated above, the quantity of aqueous alkali solution charged from line 12 is insufficient to neutralize a substantial quantity of acidic materials present in the epoxidation effluent charged to treater 11. An organic phase is removed from treater 11 through line 14.

The organic phase can be passed to treater 15, wherein it can be contacted with aqueous alkali solution charged from line 16, which is joined to line 12. Here again, an aqueous phase containing alkali salts of formic acid, benzoic acid, phenol and other acidic organic materials is formed, and an aqueous solution thereof is removed from treater 15 through line 17. This solution can be incinerated (not shown), for example, to recover the alkaline component of the original alkali solution. An organic phase formed in treater 15 is removed therefrom through line 18 for further treatment as desired.

The catalyst removal step in the sequence of processing steps after epoxidation is not critical. For example, the catalyst removal step can be carried out before or after removal of propylene or of propylene oxide from the epoxidation effluent. Preferably, this step is carried out after substantial removal of propylene and before removal of propylene oxide.

The invention is illustrated by the following typical examples and comparative examples.

EXAMPLES 1–5

Ethylbenzene is oxidized with air at 140° C. The resulting solution is concentrated by evaporation to 17 weight percent of ethylbenzene hydroperoxide. This hydroperoxide solution is used to epoxidize propylene in the liquid phase for 75 minutes at 115° C., using feed concentration of 27 weight percent of propylene and 0.003 weight percent of dissolved molybdenum. The conversion of the hydroperoxide is about 99.5 percent, with a yield of 84 gram-mols of propylene oxide per 100 gram-mols of ethylbenzene hydroperoxide reacted. After epoxidation, the unreacted propylene is removed by distillation. The remaining epoxidation effluent contains ethylbenzene, propylene oxide, acetophenone, alpha phenylethanol, organic acids, phenol and molybdenum. This effluent is analyzed and found to contain 41 parts per million (ppm) by weight of molybdenum, 0.0148 milliequivalents per gram of acids, and 0.1 weight percent of phenol.

Portions of this epoxidation effluent are mixed with portions of aqueous sodium hydroxide as shown in Table 1 below, and the resulting mixtures are stirred for 15 minutes at 40° C. using a magnetic stirrer bar. The resulting aqueous and organic phases are separated and analyzed to determine the extent of removal of molybdenum and of acids and phenol from the organic phase so separated. Results are provided in Table I.

Table I

| Example No. | Epoxidation Effluent (g.) | Caustic Solution (g.) | Wt. % NaOH in Caustic Solution | g-equivs. Na charged per g-equiv. Mo | % Removal Mo from Organic Phase | % Removal Acids and Phenol from Organic Phase |
|---|---|---|---|---|---|---|
| 1 | 700 | 12.4 | 1 | 5.1 | 97 | 29 |
| 2 | 350 | 12.4 | 1 | 10.3 | 97 | 32 |
| 3 | 1450 | 5.0 | 1 | 1.0 | 95 | 8 |
| 4 | 675 | 6.0 | 4 | 10.3 | 98 | 38 |
| 5 | 910 | 4.06 | 4 | 5.1 | 97 | 28 |

Example 3 illustrates that substantially all of the molybdenum is removed from the organic phase even when only a stoichiometric amount of sodium hydroxide is employed. Examples 2 and 4 illustrate that substantial quantities of excess sodium hydroxide over the theoretical amount effect an increase in molybdenum removal as well as in removal of acids and phenol.

EXAMPLE 6

A. One hundred grams of the same epoxidation effluent described in Examples 1–5 are mixed with 0.5 gram of 1N NaOH in a separatory funnel and shaken therein at ambient temperature (about 20° C.) for 15 minutes. A lower aqueous phase and an upper organic phase are formed therein. The phases are separated. Analyses show that 96 percent of the molybdenum and 23 percent of the acids and phenol are removed from the organic phase.

B. In this comparative example, 100 grams of the same effluent are contacted with 5 grams of 1N NaOH in the same manner as described in (A). The molybdenum is completely removed from the organic phase. In addition, 81 percent of the acids and phenol are removed from the organic phase.

EXAMPLE 7

Three hundred grams of the same epoxidation effluent described in Examples 1–5 are mixed with 1 gram of 2.9 weight percent of aqueous ammonium hydroxide (3.2 gram-equivalents of base per gram-equivalent of molybdenum). The mixture is stirred for 15 minutes at 40° C. using a magnetic stirrer bar. The resulting aqueous and organic phases are separated. Analyses show that 97 percent of the molybdenum and 17 percent of the acids and phenol are removed from the organic phase.

EXAMPLE 8 (Comparative)

One hundred grams of the same epoxidation effluent described in Example 1–5 are mixed with 1.5 grams of water. The resulting mixture is stirred for 15 minutes at 40° C. The resulting aqueous and organic phases are separated. Analyses show that 73 percent of the molybdenum is removed from the organic phase, along with 8 percent of the acids and phenol.

EXAMPLE 9

The epoxidation reaction described in Example 1 is repeated using 0.015 weight percent of dissolved tungsten as an epoxidation catalyst instead of molybdenum. After epoxidation the unreacted propylene is removed by distillation. Three hundred grams of the remaining epoxidation effluent are mixed with 2.5 grams of 1N NaOH and stirred for 15 minutes at 40° C. The resulting aqueous and organic phases are separated. Analyses show that 96 percent of the tungsten and 14 percent of the acids and phenol are removed from the organic phase.

As shown by the illustrative examples, from about 95 to about 98 percent by weight of the catalyst present in an epoxidation effluent can be removed while removing less than about 20 percent by weight of the acid/phenol components thereof.

Selective removal of catalyst while reducing acid/phenol removal to less than about 20 percent by weight is shown graphically in FIG. 2. Comparison was made on the basis of 100 grams of epoxidation effluent treated with caustic solutions identified in Examples 1–5 and with water in comparative Example 8. As shown in FIG. 2, it is possible to sacrifice complete removal of the catalyst, yet remove at least about 95% by weight thereof, and limit removal of the acid/phenol portion to less than about 20 percent by weight.

I claim:

1. In a process for preparing an oxirane compound by reacting an olefin with an organic hydroperoxide in the presence of a metal or metal-containing cayalyst, wherein a reaction effluent containing said catalyst and acidic materials is formed, wherein said reaction effluent is contacted with an aqueous basic solution to form an aqueous phase and an organic phase, and wherein said aqueous and organic phases are separated, the improvement which comprises,
   a. contacting said effluent with a quantity of an aqueous basic solution containing from about 1 to about 3 gram-equivalents of base therein per gram-equivalent of catalyst present in said effluent to remove preferentially from about 95 percent to about 98 percent by weight of said metallic catalyst from said reactor effluent and insufficient to remove more than about 20 percent by weight of the total organic acids and phenols from said reactor effluent, and
   b. contacting the organic phase so separated with a quantity of an aqueous basic solution sufficient to neutralize acidic materials therein.

2. The process of claim 1, wherein the catalyst is molybdenum.

3. A process according to claim 1, wherein the said quantity of the aqueous basic solution in (a) is insufficient to remove more than about 10 percent of said total organic acids and phenols.

4. A process according to claim 1, wherein the olefin is propylene.

5. A process according to claim 1, wherein the basic solution contains a cation selected from the group consisting of alkali or alkaline earth metals and ammonium, and an anion selected from the group consisting of hydroxide, carbonate, bicarbonate or oxide.

6. A process according to claim 1, wherein the basic solution is a solution of sodium hydroxide.

7. A process according to claim 1, wherein the basic solution is an organic compound.

* * * * *

UNITED STATES PATENT AND TRADEMARK OFFICE
CERTIFICATE OF CORRECTION

PATENT NO. : 3,988,353
DATED : October 26, 1976
INVENTOR(S) : JOHN P. SCHMIDT

It is certified that error appears in the above—identified patent and that said Letters Patent are hereby corrected as shown below:

Column 5, Table 1, Example 1: in the final column, replace "29" with --- 19 ---.

Signed and Sealed this

Twenty-ninth Day of November 1977

[SEAL]

Attest:

RUTH C. MASON
Attesting Officer

LUTRELLE F. PARKER
Acting Commissioner of Patents and Trademarks